(12) United States Patent
Larkin

(10) Patent No.: US 9,878,129 B2
(45) Date of Patent: Jan. 30, 2018

(54) INFUSION SITE RETAINER FOR MAINTAINING INFUSION TUBING

(71) Applicant: Daniel Larkin, St. Paul, MN (US)

(72) Inventor: Daniel Larkin, St. Paul, MN (US)

( * ) Notice: Subject to any disclaimer, the term of this patent is extended or adjusted under 35 U.S.C. 154(b) by 817 days.

(21) Appl. No.: 14/277,467

(22) Filed: May 14, 2014

(65) Prior Publication Data
US 2014/0343531 A1 Nov. 20, 2014

Related U.S. Application Data

(60) Provisional application No. 61/823,132, filed on May 14, 2013.

(51) Int. Cl.
A61M 25/02 (2006.01)

(52) U.S. Cl.
CPC ....... *A61M 25/02* (2013.01); *A61M 2025/024* (2013.01); *A61M 2025/028* (2013.01)

(58) Field of Classification Search
CPC ............ A61M 25/02; A61M 2025/024; A61M 2025/028
USPC ........................................................ 604/178
See application file for complete search history.

(56) References Cited

U.S. PATENT DOCUMENTS

| | | | |
|---|---|---|---|
| 3,363,864 A | 1/1968 | Hanger | |
| 3,630,195 A * | 12/1971 | Santomieri | A61M 25/02 128/DIG. 26 |
| 4,029,103 A * | 6/1977 | McConnell | A61M 25/02 128/DIG. 26 |
| 4,397,641 A | 8/1983 | Jacobs | |
| 4,419,094 A * | 12/1983 | Patel | A61M 25/06 128/DIG. 26 |
| 4,605,397 A * | 8/1986 | Ligon | A61M 5/1408 128/DIG. 26 |
| 4,857,058 A * | 8/1989 | Payton | A61M 25/02 128/DIG. 26 |
| 5,147,320 A * | 9/1992 | Reynolds | A61M 25/02 604/174 |
| 5,167,240 A | 12/1992 | Rozier et al. | |
| D335,926 S | 5/1993 | Rozier et al. | |
| 5,456,671 A | 10/1995 | Bierman | |
| D375,355 S | 11/1996 | Bierman | |
| 5,643,217 A * | 7/1997 | Dobkin | A61B 17/00 604/174 |
| 5,690,617 A * | 11/1997 | Wright | A61M 25/02 128/DIG. 26 |
| 5,702,371 A | 12/1997 | Bierman | |
| D389,911 S | 1/1998 | Bierman | |
| 5,800,402 A | 9/1998 | Bierman | |
| 5,806,516 A | 9/1998 | Beattie | |
| D424,692 S | 5/2000 | Monaghan et al. | |
| 6,134,754 A | 10/2000 | Hansson et al. | |

(Continued)

FOREIGN PATENT DOCUMENTS

| | | |
|---|---|---|
| CA | 2732511 | 11/2009 |
| EP | 0916361 A1 | 5/1999 |
| WO | 2009137607 A1 | 11/2009 |

*Primary Examiner* — Theodore Stigell
(74) *Attorney, Agent, or Firm* — Dicke, Billig & Czaja, PLLC

(57) ABSTRACT

An infusion site retainer configured to maintain tubing coupled to an infusion port includes a base configured to be secured to a patient and comprises a patient surface opposite a first surface. At least one trench is formed in the base to couple the tubing to the base.

10 Claims, 7 Drawing Sheets

(56) References Cited

U.S. PATENT DOCUMENTS

| | | | |
|---|---|---|---|
| 6,500,154 B1 | 12/2002 | Hakky et al. | |
| 6,526,981 B1 | 3/2003 | Rozier et al. | |
| 6,786,892 B2 * | 9/2004 | Bierman | A61M 25/02 128/DIG. 26 |
| D622,840 S | 8/2010 | Heitkamp | |
| 8,123,681 B2 | 2/2012 | Schaeffer | |
| 8,394,067 B2 | 3/2013 | Bracken et al. | |
| 8,821,449 B1 * | 9/2014 | Bass | A61J 15/0061 604/180 |
| 2005/0215979 A1 | 9/2005 | Kornerup et al. | |
| 2006/0270994 A1 * | 11/2006 | Bierman | A61M 25/02 604/180 |
| 2007/0129685 A2 | 6/2007 | Bierman | |
| 2008/0071224 A1 | 3/2008 | Forsyth | |
| 2008/0119792 A1 | 5/2008 | Kornerup et al. | |
| 2009/0105656 A1 | 4/2009 | Schaeffer | |
| 2009/0281502 A1 | 11/2009 | Heitkamp | |
| 2009/0326456 A1 | 12/2009 | Cross et al. | |
| 2009/0326472 A1 | 12/2009 | Carter et al. | |
| 2010/0022956 A1 | 1/2010 | Tipsmark et al. | |
| 2010/0298778 A1 | 11/2010 | Bracken et al. | |
| 2011/0054409 A1 | 3/2011 | Nishtala | |
| 2013/0018319 A1 * | 1/2013 | Abe | A61M 25/02 604/174 |
| 2013/0165863 A1 * | 6/2013 | Nilson | A61M 25/02 604/180 |
| 2014/0148778 A1 * | 5/2014 | Levy | A61M 25/02 604/500 |

\* cited by examiner

INFUSION SITE RETAINER FOR MAINTAINING INFUSION TUBING

CROSS-REFERENCE TO RELATED APPLICATION

This Non-Provisional patent application claims the benefit of the filing date of U.S. Provisional Patent Application Ser. No. 61/823,132 filed May 14, 2013, entitled "INFUSION SITE RETAINER FOR MAINTAINING INFUSION TUBING", which is hereby incorporated by reference herein.

BACKGROUND OF THE INVENTION

Intravenous infusion is the introduction of a liquid, such as a saline solution, into a vein of a patient for the therapeutic treatment of the patient. The intravenous infusion is introduced to a body site through an infusion port that generally has a needle suited for accessing the vein and tubing extending from the infusion port that communicates with a fluid receptacle, such as a sealed plastic bag.

Intravenous infusion is a common medical practice that is done in outpatient procedures, inpatient and other surgical procedures, and long-term care procedures. Some patients are sedated and move in an involuntary manner that has the potential to disrupt or remove the infusion port from the infusion site. Other patients are uncomfortable with the notion of intravenous infusion and are fearful that their voluntary movements might displace the infusion port. Still other patients are confused or agitated and pull at the tubing connected to the infusion port.

For therapeutic and other reasons, it is desirable to provide improved healthcare outcomes for patients undergoing intravenous infusion.

SUMMARY OF THE INVENTION

One embodiment is directed to an infusion site retainer configured to maintain tubing coupled to an infusion port. The infusion site retainer includes a base configured to be secured to a patient and comprises a patient surface opposite a first surface. At least one trench is formed in the base to couple the tubing to the base.

DETAILED DESCRIPTION OF THE INVENTION

Figure 1:
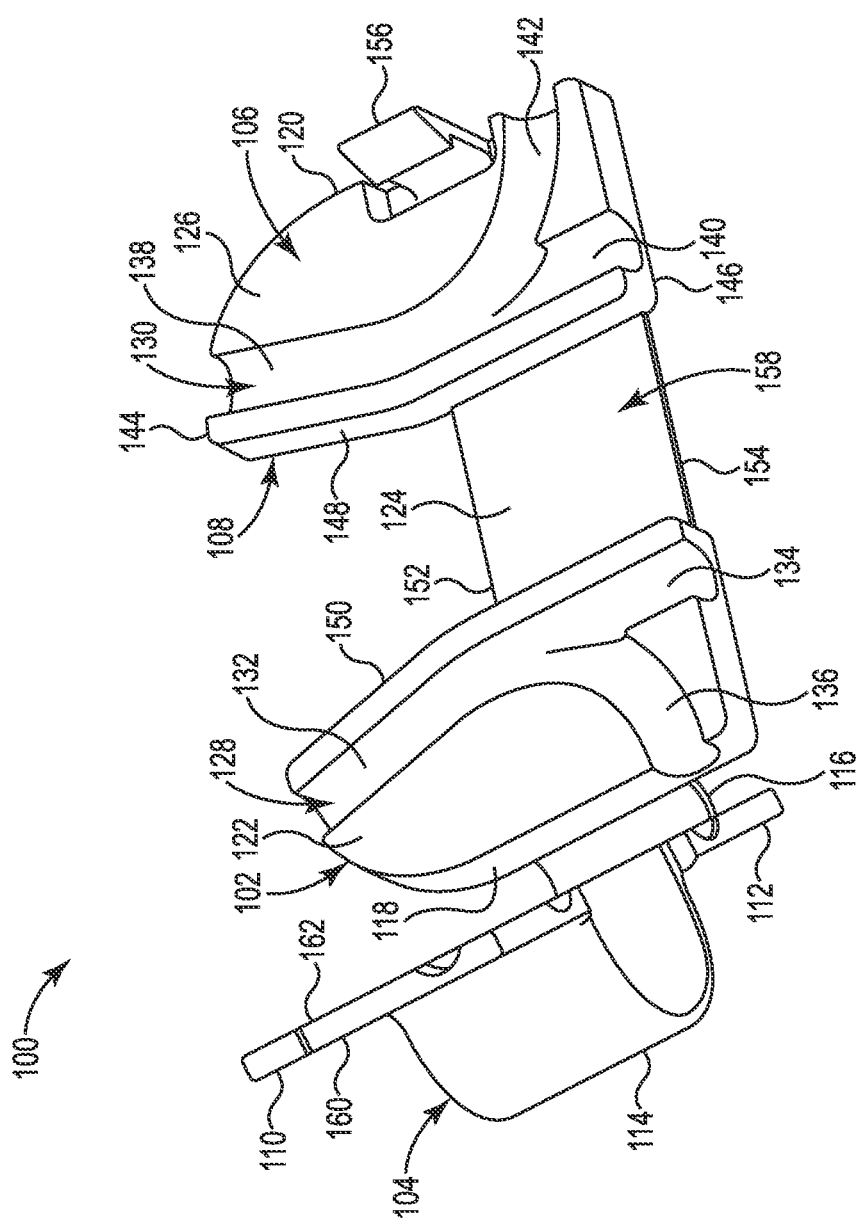
FIG. 1 is a diagram illustrating a first perspective view of an infusion site retainer according to one embodiment.

FIG. 1 is a diagram illustrating a first perspective view of an infusion site retainer 100 according to one embodiment. Infusion site retainer 100 includes a base 102 and a cover 104. Base 102 is attachable to a patient. In one embodiment, infusion site retainer 100 is provided as a stand-alone component that is attached to the limb of the patient in any manner deemed suitable by the healthcare provider.

Base 102 includes a first surface or top surface 106 opposite a patient surface or bottom surface 108. In one embodiment, patient surface 108 includes an adhesive configured to attach base 102 to the patient. In one form of this embodiment, the adhesive is initially covered by a cover layer that can be easily peeled off when the retainer 100 is about to be applied to a patient. Base 102 includes opposing first and second lateral sides 118, 120, and a proximal end 146 opposite a distal end 144.

Base 102 includes first lateral base portion 122, central base portion 124, and second lateral base portion 126. Central base portion 124 is positioned between first lateral base portion 122 and second lateral base portion 126. Central base portion 124 extends between an inner sidewall 150 of first lateral base portion 122 and an inner sidewall 148 of second lateral base portion 126. First lateral base portion 122 and second lateral base portion 126 have a larger height (thickness) than central base portion 124 such that the sidewalls 148 and 150 and the top surface 106 of central base portion 124 define a channel 158. The channel 158 extends from a proximal end 154 of central base portion 124 to a distal end 152 of central base portion 124.

In one embodiment, base 102 has a length extending between ends 144, 146 of approximately 3.5 cm and a width extending between sides 118, 120 of about 3.5 cm. In another embodiment, base 102 has a length extending between ends 144, 146 of approximately 2 cm and a width extending between sides 118, 120 of about 5 cm. In yet another embodiment, base 102 has a length extending between ends 144, 146 of approximately 5 cm and a width extending between sides 118, 120 of about 6 cm. In one form of this embodiment, each of base portions 122, 124, and 126 has a width of about 2 cm, and base portions 122 and 126 have a length of about 5 cm, and base portion 124 has length of about 3 cm. In one embodiment, base portions 122 and 126 have a height or thickness of about 4 mm, and base portion 124 has a height or thickness of about 0.5 mm. Other embodiments may have different dimensions.

First lateral base portion 122 includes a trench 128 formed in the first surface 106 of the base portion 122. Trench 128 includes a first a first trench portion 132 that extends from the distal end 144 of the base 102 toward the proximal end 146 of the base 102. First trench portion 132 branches into a second trench portion 134 and a third trench portion 136. In one embodiment, second trench portion 134 is substantially parallel to first trench portion 132, or is slightly angled with respect to first trench portion 132. Second trench portion 134 extends from first trench portion 132 to the proximal end 146 of the base 102. Third trench portion 136 curves laterally away from first trench portion 132, and is substantially perpendicular to first trench portion 132 and second trench portion 134. Third trench portion 136 extends from first trench portion 132 to the lateral side 118 of the base 102.

Second lateral base portion 126 includes a trench 130 formed in the first surface 106 of the base portion 126. Trench 130 includes a first a first trench portion 138 that extends from the distal end 144 of the base 102 toward the proximal end 146 of the base 102. First trench portion 138 branches into a second trench portion 140 and a third trench portion 142. In one embodiment, second trench portion 140 is substantially parallel to first trench portion 138, or is slightly angled with respect to first trench portion 138. Second trench portion 140 extends from first trench portion 138 to the proximal end 146 of the base 102. Third trench portion 142 curves laterally away from first trench portion 138, and is substantially perpendicular to first trench portion 138 and second trench portion 140. Third trench portion 142 extends from first trench portion 138 to the lateral side 120 of the base 102.

In one embodiment, base 102 is integrally formed from a recyclable or biodegradable plastic to include trenches 128 and 130. Trench 128 is configured to couple a first portion of the infusion tubing to base 102, and trench 130 is configured to couple a second portion of the infusion tubing to base 102. In one embodiment, trenches 128 and 130 are configured to secure the first and second portions of the tubing in a substantially immobile relationship relative to the base 102, without crimping the tubing. For trench 128, the first portion of the infusion tubing may be secured in the first trench portion 132 and the second trench portion 134 to maintain the first portion of the tubing substantially straight or at a slight angle. Alternatively, the first portion of the infusion tubing may be secured in the first trench portion 132 and the third trench portion 136. Similarly, for trench 130, the second portion of the infusion tubing may be secured in the first trench portion 138 and the second trench portion 140 to maintain the second portion of the tubing substantially straight or at a slight angle. Alternatively, the second portion of the infusion tubing may be secured in the first trench portion 138 and the third trench portion 142.

In one embodiment, trenches 128 and 130 have a semi-circular cross-sectional shape, and are sized to enable the infusion tubing to be pressed into the trenches 128 and 130 in a manner that captures the infusion tubing. In one embodiment, the trenches 128 and 130 are configured to clamp down upon or grab the infusion tubing, and in this manner prevent the infusion tubing from tugging on the infusion port.

Figure 2:
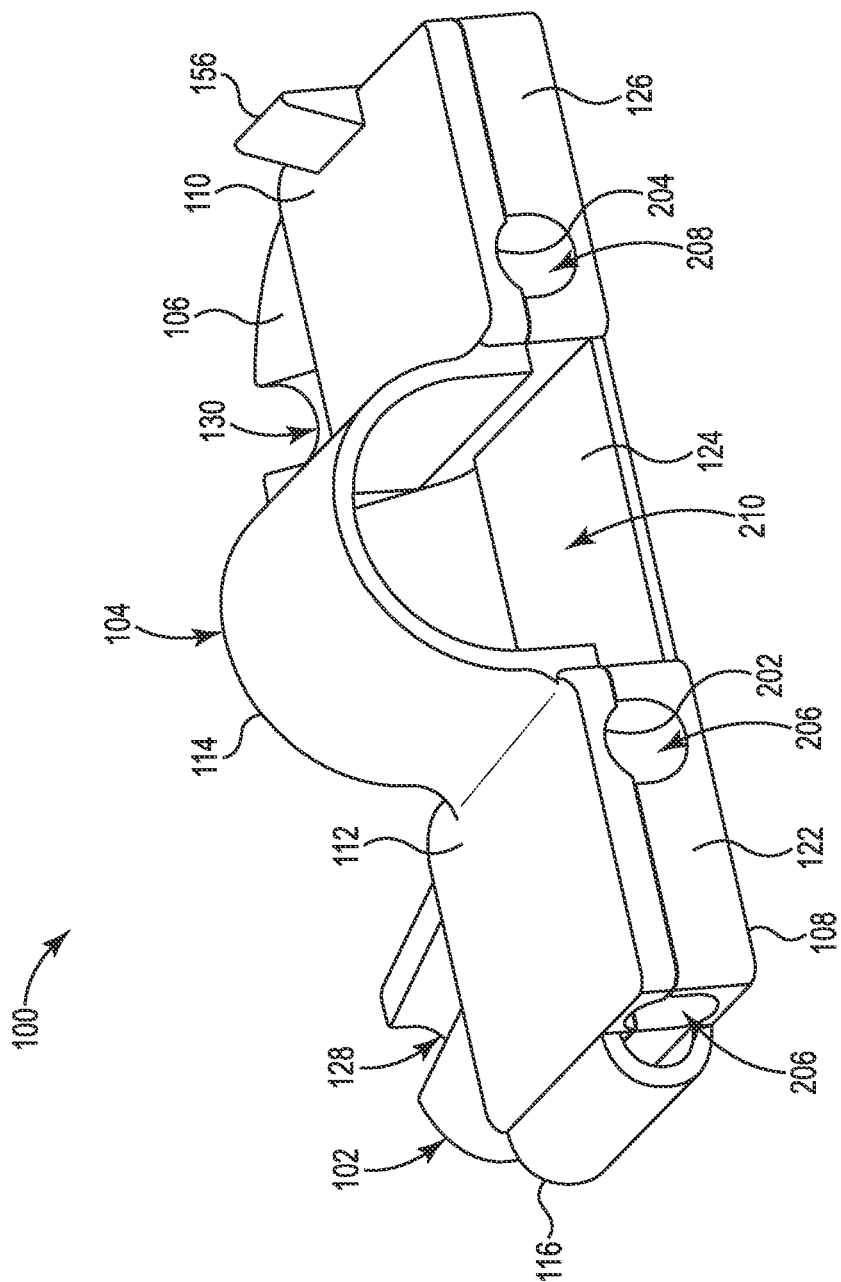
FIG. 2 is a diagram illustrating a second perspective view of the infusion site retainer shown in FIG. 1 according to one embodiment.
Figure 3:
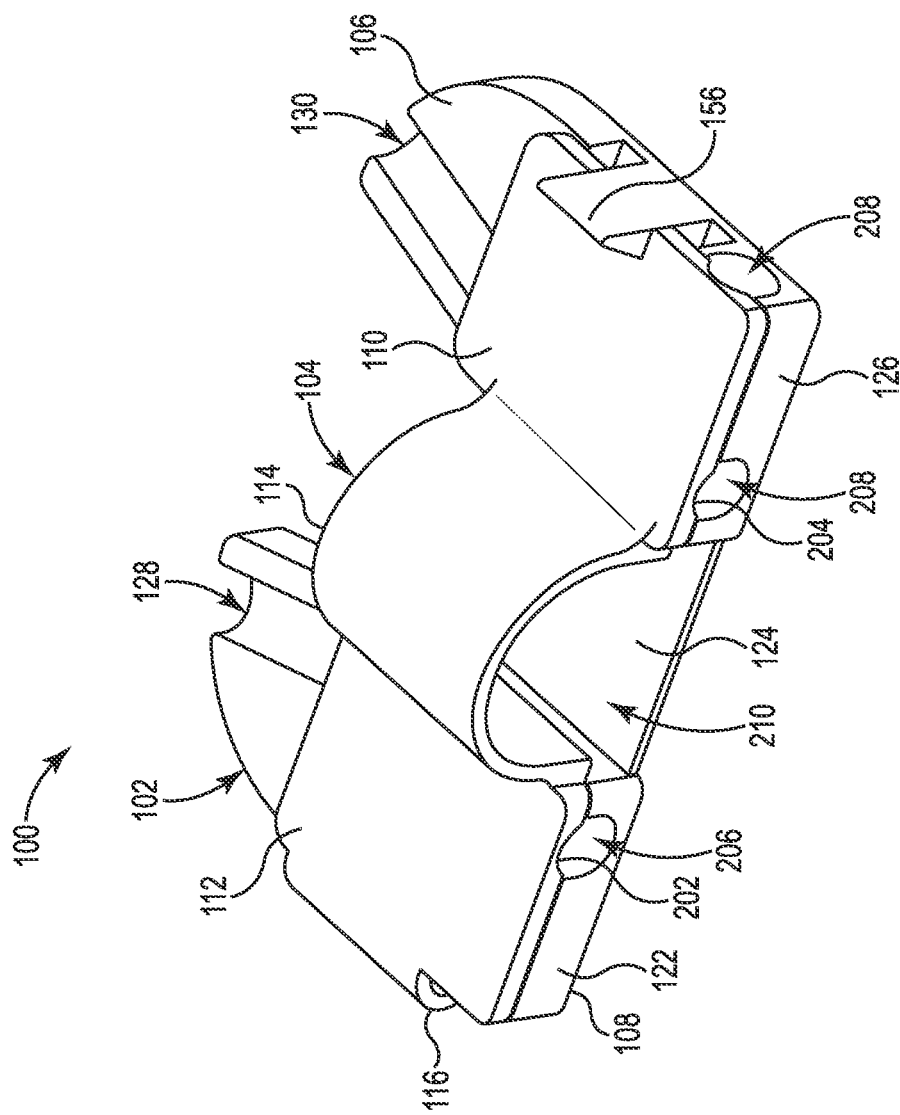
FIG. 3 is a diagram illustrating a third perspective view of the infusion site retainer shown in FIG. 1 according to one embodiment.

Cover 104 includes a first cover portion 110, a second cover portion 112, and a semi-cylindrical protrusion 114. Protrusion 114 is positioned between first cover portion 110 and second cover portion 112. Cover 104 has a top surface 160 and a bottom surface 162. Cover 104 also includes a hinge attachment feature 116 that pivotally connects the cover 104 to the lateral side 118 of the base 102. Cover 104 is configured to be pivoted via hinge attachment feature 116 between an open position as shown in FIG. 1 and a closed position as shown in FIGS. 2 and 3. Cover 104 may be maintained in the closed position via a clip 156 on the lateral side 120 of the base 102. After closing the cover 104, the clip 156 is snapped over the top surface 160 of the first cover portion 110 to hold the cover 104 in the closed position. The cover 104 is closed after the tubing is inserted into the trenches 128 and 130 to help secure the tubing in the base 102. Other embodiments may not include a cover. In retainers with a cover 104 according to one embodiment, the trenches 128 and 130 are about 3 mm deep to accommodate standard 3 mm diameter tubing, and in retainers without a cover 104 according to one embodiment, the trenches 128 and 130 are about 4 mm deep.

The infusion site retainer 100 is attached to the patient by a healthcare worker in a suitable clean or antiseptic manner before or after the healthcare worker introduces an infusion port to the patient at the infusion site. The infusion port includes a needle that is introduced to a vein (or broadly, to the circulatory system of the patient). Infusion tubing extends from the infusion port to an infusion reservoir, which is typically a plastic bag containing infusion liquid.

FIG. 2 is a diagram illustrating a second perspective view of the infusion site retainer 100 shown in FIG. 1 according to one embodiment. FIG. 3 is a diagram illustrating a third perspective view of the infusion site retainer shown in FIG. 1 according to one embodiment. In FIGS. 2 and 3, cover 104 is in a closed position. In the closed position, cover 104 laterally extends across the entire base 102 from the lateral side 118 to the lateral side 120 (FIG. 1), and longitudinally extends from the proximal end 146 to about the middle of the first trench portions 132 and 138 (FIG. 1).

Trenches 202 and 204 are formed in the bottom surface 162 of the cover 104. Trenches 202 and 204 have a semi-circular cross-sectional shape, and are shallower than trenches 128 and 130 in the illustrated embodiment. In the closed position, trench 202 is aligned with and lies directly over trench 128, and the combination of trench 202 and trench 128 forms a tunnel 206 with a substantially circular cross section. In the closed position, trench 204 is aligned with and lies directly over trench 130, and the combination of trench 204 and trench 130 forms a tunnel 208 with a substantially circular cross section.

In the closed position, a tunnel 210 is also formed, which is defined by the semi-cylindrical protrusion 114, the central base portion 124, and the sidewalls 148 and 150. The tunnel 210 extends between proximal end 154 of central base portion 124 and distal end 152 of central base portion 124. The tunnel 210 is sized to receive a needle or infusion port.

Figure 4:
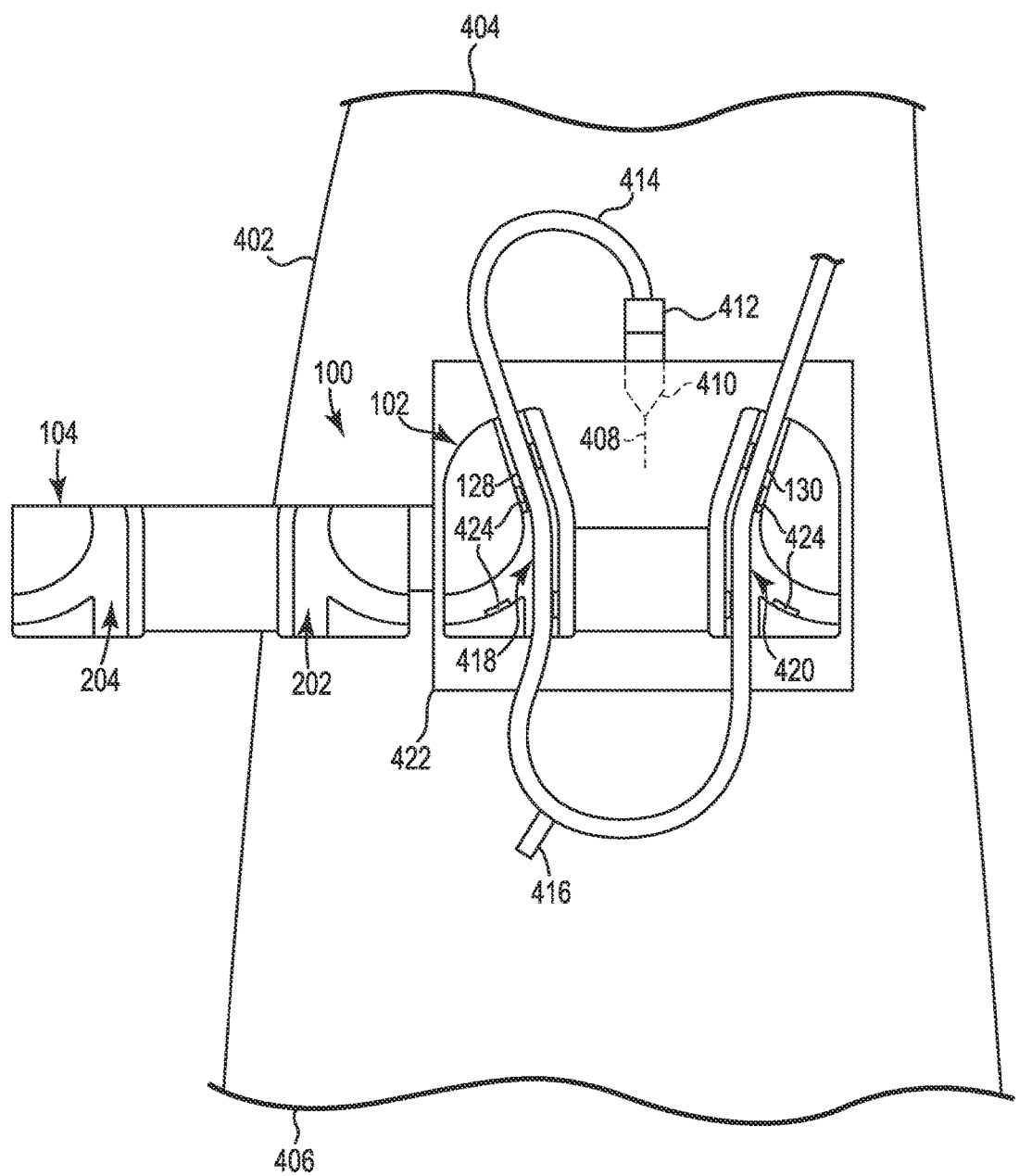
FIG. 4 is a diagram illustrating a top view of the infusion site retainer shown in FIG. 1 attached to a patient's arm according to one embodiment.

FIG. 4 is a diagram illustrating a top view of the infusion site retainer 100 shown in FIG. 1 attached to a patient's arm 402 according to one embodiment. Arm 402 includes a distal region 404 closer to the patient's hand, and a proximal region 406 farther away from the patient's hand. A needle 408 is inserted into the patient's arm 402 and is coupled to an infusion port 410. Infusion tubing 414 includes a connector 412 configured to be coupled to the infusion port 410. The infusion tubing 414 also includes an infusion port 416 for the introduction of fluids into the patient. The infusion tubing 414 is shown with a smaller diameter in FIGS. 4 and 5 than it would actually appear to allow the infusion tubing elements to be more easily distinguished from the elements of the infusion site retainer 100 and 500.

A film dressing 422 is applied to the arm and covers the needle 408 and a portion of the infusion port 410 (as shown by the dashed lines). In one embodiment, the film dressing 422 is a Tegaderm™ film dressing. The infusion site retainer 100 is adhesively attached to a top surface of the film dressing 422 adjacent to the needle 408.

A first portion 418 of the infusion tubing 414 has been inserted into the trench 128 of the first base portion 122, and a second portion 420 of the infusion tubing 414 has been inserted into the trench 130 of the second base portion 126. More specifically, the first portion 418 of the infusion tubing 414 has been inserted into the first trench portion 132 and the second trench portion 134, and the second portion 420 of the infusion tubing 414 has been inserted into the first trench portion 138 and the second trench portion 140. Alternatively, one or both of the third trench portions 136 and 142 may be used. In the illustrated embodiment, the infusion site retainer 100 includes locking features 424 that help lock the tubing 414 in place in the trenches 128 and 130. Each of the locking features 424 extends over and covers a small portion of one of the trenches 128 and 130. In the illustrated embodiment, four locking features 424 are used for each of the trenches 128 and 130, with the locking features 424 being positioned on alternating sides of the trench along the length of the trench. The cover 104 may be closed over the base 102 to further secure the infusion tubing 414 in place.

Figure 5:
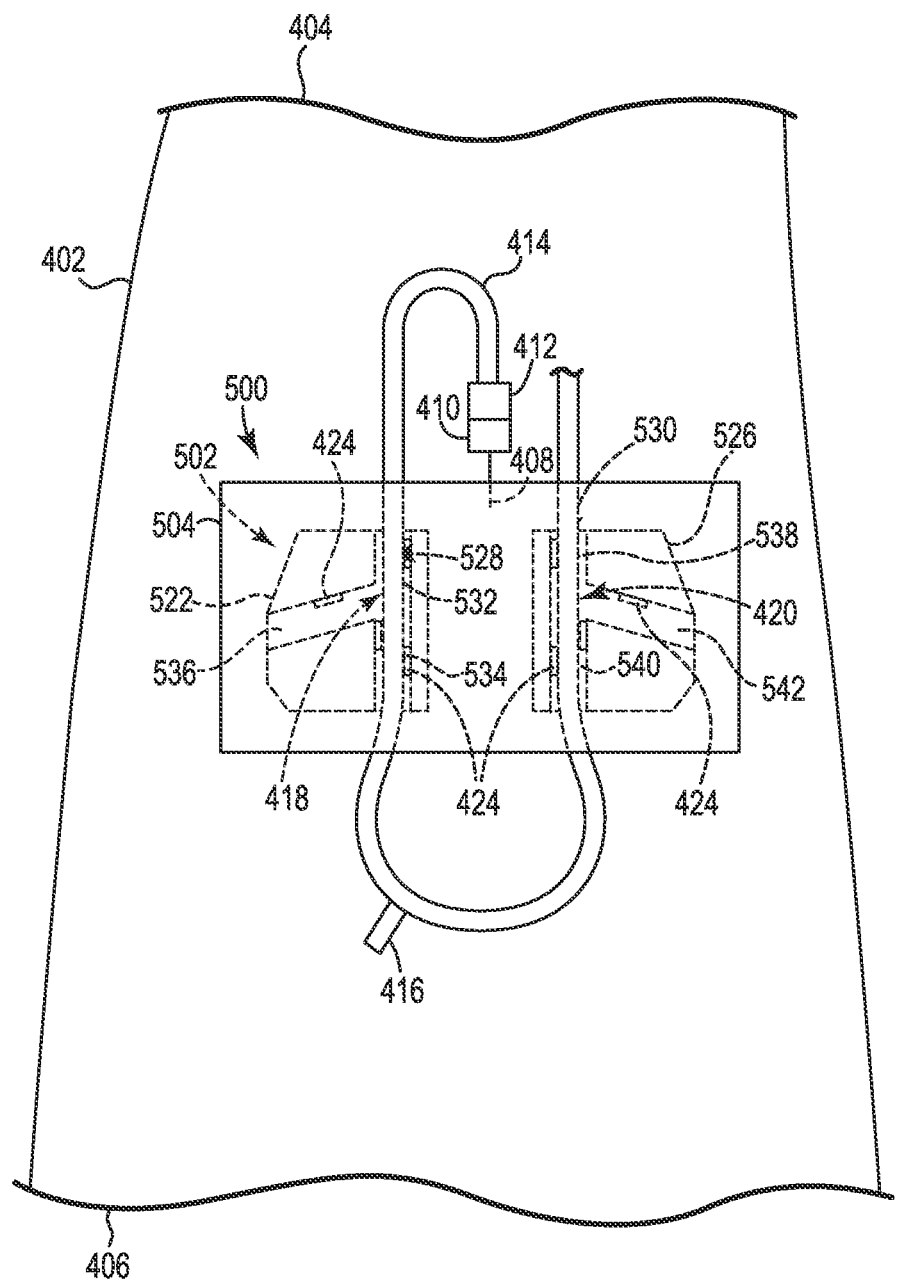
FIG. 5 is a diagram illustrating a top view of an infusion site retainer attached to a patient's arm according to another embodiment.

FIG. 5 is a diagram illustrating a top view of an infusion site retainer 500 attached to a patient's arm 402 according to another embodiment. Arm 402 includes a distal region 404 closer to the patient's hand, and a proximal region 406 farther away from the patient's hand. A needle 408 is inserted into the patient's arm 402 and is coupled to an infusion port 410. Infusion tubing 414 includes a connector 412 configured to be coupled to the infusion port 410. The infusion tubing 414 also includes an infusion port 416 for the introduction of fluids into the patient.

Infusion site retainer 500 includes a base 502 and a cover 504. Base 502 is attachable to a patient. Base 502 includes a first surface or top surface opposite a patient surface or bottom surface. In one embodiment, the patient surface includes an adhesive configured to attach base 502 to the patient. In one form of this embodiment, the adhesive is covered by a cover layer that can be easily peeled off when the retainer 500 is about to be applied to a patient.

Base 502 includes first lateral base portion 522 and second lateral base portion 526, which are separate and distinct elements in the illustrated embodiment. In one embodiment, base 502 has dimensions that are similar to those of the base 102 described above.

First lateral base portion 522 includes a trench 528 formed in the top surface of the base portion 522. Trench 528 includes a first a first trench portion 532 that extends from the distal end of the base 502 toward the proximal end of the base 502. First trench portion 532 branches into a second trench portion 534 and a third trench portion 536. In the illustrated embodiment, second trench portion 534 is substantially parallel to first trench portion 532. Second trench portion 534 extends from first trench portion 532 to the proximal end of the base 502. Third trench portion 536 branches laterally away from first trench portion 532, and is close to perpendicular to first trench portion 532 and second trench portion 534. Third trench portion 536 extends from first trench portion 532 to the lateral side of the base 502.

Second lateral base portion 526 includes a trench 530 formed in the top surface of the base portion 526. Trench 530 includes a first a first trench portion 538 that extends from the distal end of the base 502 toward the proximal end of the base 502. First trench portion 538 branches into a second trench portion 540 and a third trench portion 542. In the illustrated embodiment, second trench portion 540 is substantially parallel to first trench portion 538. Second trench portion 540 extends from first trench portion 538 to the proximal end of the base 502. Third trench portion 542 branches laterally away from first trench portion 538, and is close to perpendicular to first trench portion 538 and second trench portion 540. Third trench portion 542 extends from first trench portion 538 to the lateral side of the base 502.

In one embodiment, base 502 is integrally formed from a recyclable or biodegradable plastic to include trenches 528 and 530. Trench 528 is configured to couple a first portion of the infusion tubing to base 502, and trench 530 is configured to couple a second portion of the infusion tubing to base 502. In one embodiment, trenches 528 and 530 are configured to secure the first and second portions of the tubing in a substantially immobile relationship relative to the base 502, without crimping the tubing.

For trench 528, the first portion of the infusion tubing may be secured in the first trench portion 532 and the second trench portion 534 to maintain the first portion of the tubing substantially straight or at a slight angle. Alternatively, the first portion of the infusion tubing may be secured in the first trench portion 532 and the third trench portion 536, which forms a larger curve in the infusion tubing. Similarly, for trench 530, the second portion of the infusion tubing may be secured in the first trench portion 538 and the second trench portion 540 to maintain the second portion of the tubing substantially straight or at a slight angle. Alternatively, the second portion of the infusion tubing may be secured in the first trench portion 538 and the third trench portion 542, which forms a larger curve in the infusion tubing.

In one embodiment, trenches 528 and 530 have a semicircular cross-sectional shape, and are sized to enable the infusion tubing to be pressed into the trenches 528 and 530 in a manner that captures the infusion tubing. In one embodiment, the trenches 528 and 530 are configured to clamp down upon or grab the infusion tubing, and in this manner prevent the infusion tubing from tugging on the infusion port.

In the illustrated embodiment, a first portion 418 of the infusion tubing 414 has been inserted into the trench 528 of the first base portion 522, and a second portion 420 of the infusion tubing 414 has been inserted into the trench 530 of the second base portion 526. More specifically, the first portion 418 of the infusion tubing 414 has been inserted into the first trench portion 532 and the second trench portion 534, and the second portion 420 of the infusion tubing 414 has been inserted into the first trench portion 538 and the second trench portion 540. Alternatively, one or both of the third trench portions 536 and 542 may be used. In the illustrated embodiment, the infusion site retainer 500 includes locking features 424 that help lock the tubing 414 in place in the trenches 528 and 530. Each of the locking features 424 extends over and covers a small portion of one of the trenches 528 and 530. In the illustrated embodiment, four locking features 424 are used for each of the trenches 528 and 530, with the locking features 424 being positioned on alternating sides of the trench along the length of the trench.

In one embodiment, cover 504 is very flexible and substantially transparent or translucent, and includes an adhesive surface configured to be attached to the patient's arm 402. In one embodiment, the cover 504 is a Tegaderm™ film dressing. In the illustrated embodiment, cover 504 completely covers the base portions 522 and 526, covers the portions of the infusion tubing inserted into the base portions 522 and 526, and covers the infusion needle 408, so all of these portions are shown with dashed lines. The cover 504 is applied after the tubing is inserted into the trenches 528 and 530 to help secure the tubing in the base 502. Other embodiments may not include a cover.

The infusion site retainer 500 is attached to the patient by a healthcare worker in a suitable clean or antiseptic manner before or after the healthcare worker introduces an infusion port to the patient at the infusion site. The infusion port includes a needle that is introduced to a vein (or broadly, to the circulatory system of the patient). Infusion tubing extends from the infusion port to an infusion reservoir, which is typically a plastic bag containing infusion liquid.

Figure 6A:
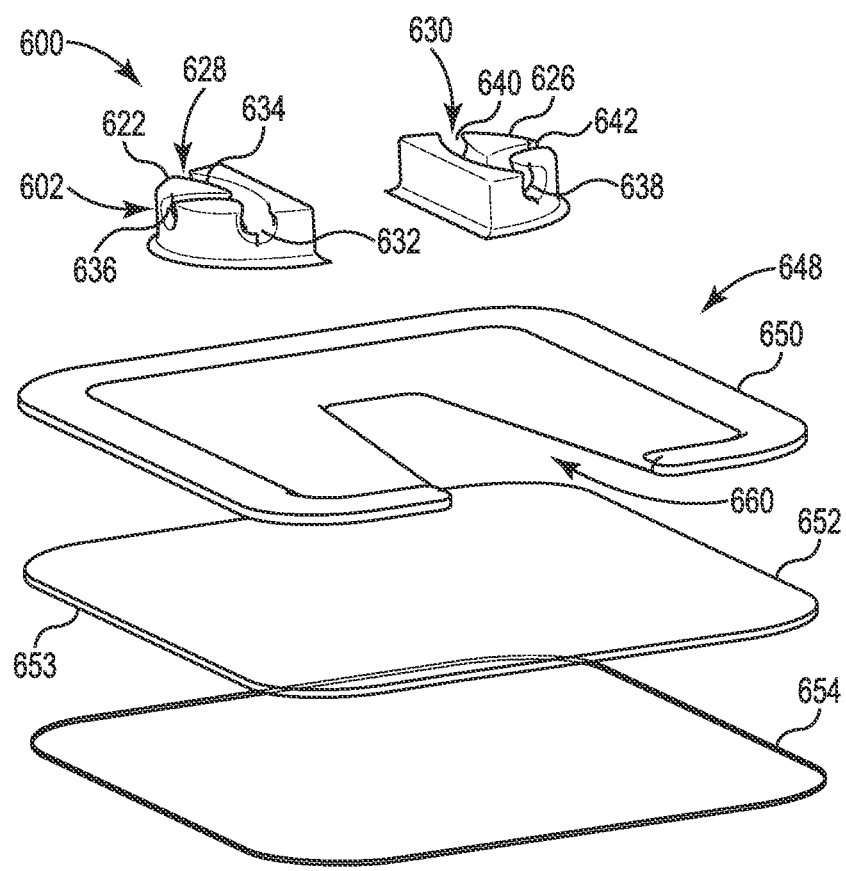
FIG. 6A is a diagram illustrating an assembly view of an infusion site retainer according to another embodiment.

FIG. 6A is a diagram illustrating an assembly view of an infusion site retainer 600 according to another embodiment. Infusion site retainer 600 includes a base 602, and a multi-layer support structure 648. The base 602 is attachable to the support structure 648, and the support structure 648 is attachable to a patient. Support structure 648 includes a fabric layer 650, a clear plastic layer 652, and a cover layer 654. In one embodiment, the cover layer 654 is a clear plastic film. A bottom surface of the fabric layer 650 is configured to be attached to a top surface of the clear plastic layer 652. A bottom surface of the clear plastic layer 652 is configured to be attached to a top surface of the cover layer 654. In one embodiment, the bottom surface of the clear plastic layer 652 comprises an adhesive surface 653, which is initially covered by the cover layer 654. The cover layer 654 is easily removable by a user, to expose the adhesive surface 653, and allow the adhesive surface 653 to be attached to a patient's arm.

Base 602 includes a top surface opposite a bottom surface. In one embodiment, the bottom surface includes an adhesive configured to attach base 602 to the support structure 648. Base 602 includes first lateral base portion 622 and second lateral base portion 626, which are separate and distinct elements in the illustrated embodiment. In one embodiment, base 602 has dimensions that are similar to those of the base 102 described above.

First lateral base portion 622 includes a trench 628 formed in the top surface of the base portion 622. Trench 628 includes a first a first trench portion 632 that extends from the distal end of the base 602 toward the proximal end of the base 602. First trench portion 632 branches into a second trench portion 634 and a third trench portion 636. Second trench portion 634 extends from first trench portion 632 to the proximal end of the base 602. Third trench portion 636 branches laterally away from first trench portion 632, and is close to perpendicular to first trench portion 632 and second trench portion 634. Third trench portion 636 extends from first trench portion 632 to the lateral side of the base 602.

Second lateral base portion 626 includes a trench 630 formed in the top surface of the base portion 626. Trench 630 includes a first a first trench portion 638 that extends from the distal end of the base 602 toward the proximal end of the base 602. First trench portion 638 branches into a second trench portion 640 and a third trench portion 642. Second trench portion 640 extends from first trench portion 638 to the proximal end of the base 602. Third trench portion 642 branches laterally away from first trench portion 638, and is close to perpendicular to first trench portion 638 and second trench portion 640. Third trench portion 642 extends from first trench portion 638 to the lateral side of the base 602. Trench portions 632, 634, 636, 638, 640, and 642 are all curved along their length.

In one embodiment, base 602 is integrally formed from a recyclable or biodegradable plastic to include trenches 628 and 630. Base 602 according to one embodiment is formed from a thermoplastic elastomer. Trench 628 is configured to couple a first portion of the infusion tubing to base 602, and trench 630 is configured to couple a second portion of the infusion tubing to base 602. In one embodiment, trenches 628 and 630 are configured to secure the first and second portions of the tubing in a substantially immobile relationship relative to the base 602, without crimping the tubing.

For trench 628, the first portion of the infusion tubing may be secured in the first trench portion 632 and the second trench portion 634 to maintain the first portion of the tubing substantially straight, but with a small curve. Alternatively, the first portion of the infusion tubing may be secured in the first trench portion 632 and the third trench portion 636, which forms a larger curve in the infusion tubing. Similarly, for trench 630, the second portion of the infusion tubing may be secured in the first trench portion 638 and the second trench portion 640 to maintain the second portion of the tubing substantially straight, but with a small curve. Alternatively, the second portion of the infusion tubing may be secured in the first trench portion 638 and the third trench portion 642, which forms a larger curve in the infusion tubing.

In one embodiment, trenches 628 and 630 have a semi-circular cross-sectional shape, and are sized to enable the infusion tubing to be pressed into the trenches 628 and 630 in a manner that captures the infusion tubing. In one embodiment, the trenches 628 and 630 are configured to clamp down upon or grab the infusion tubing, and in this manner prevent the infusion tubing from tugging on the infusion port.

The infusion site retainer 600 is attached to the patient by a healthcare worker in a suitable clean or antiseptic manner before or after the healthcare worker introduces an infusion port to the patient at the infusion site. The infusion port includes a needle that is introduced to a vein (or broadly, to the circulatory system of the patient). Infusion tubing extends from the infusion port to an infusion reservoir, which is typically a plastic bag containing infusion liquid.

Figure 6B:
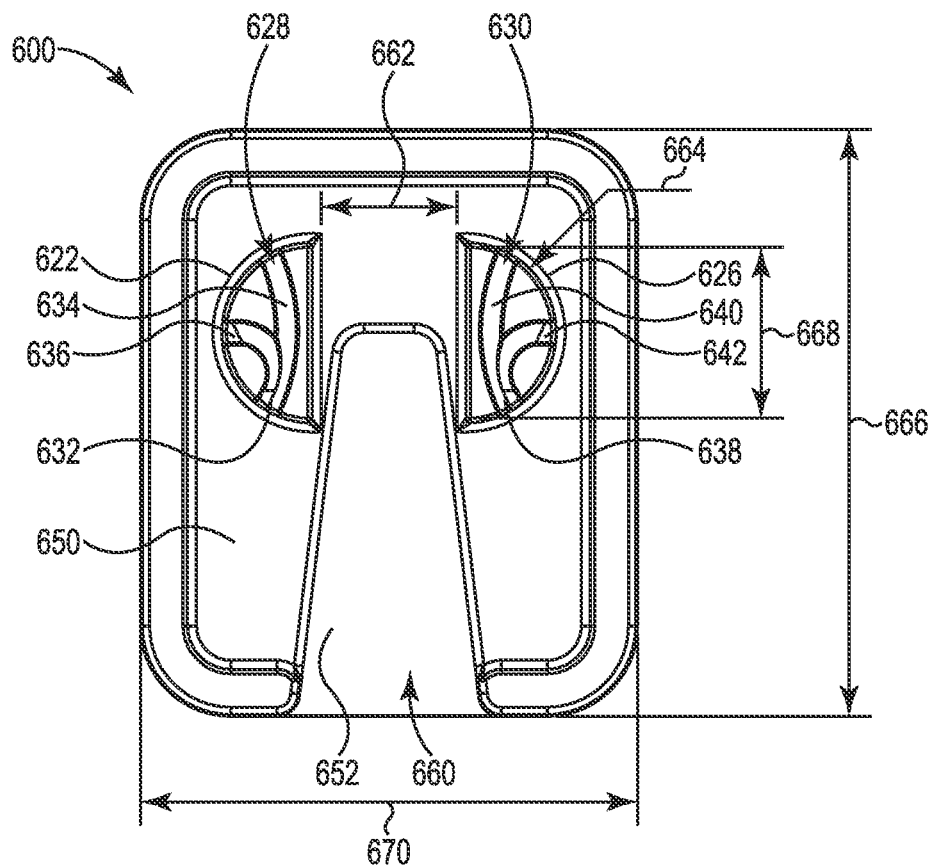
FIG. 6B is a diagram illustrating a top view of the infusion site retainer shown in FIG. 6A after assembly according to one embodiment.

FIG. 6B is a diagram illustrating a top view of the infusion site retainer 600 shown in FIG. 6A after assembly according to one embodiment. As shown in FIG. 6B, each of the base portions 622 and 626 has a semi-circular shape, with a straight side and a rounded side. The straight sides of the base portions 622 and 626 are parallel and face each other, and are separated by a distance 662, which is about 1.905 cm in one embodiment. The top surfaces of the base portions 622 and 626 have a radius of curvature 664, which is about 1.270 cm in one embodiment. The base portions 622 and 626 have a length 668, which is about 2.410 cm in one embodiment. The support structure 648 has a length 666, which is about 8.255 cm in one embodiment, and a width 670, which is about 6.985 cm in one embodiment.

An opening 660 is formed in one side of the fabric layer 650, and extends toward and beyond the center of the fabric layer 650. The width of the opening 660 becomes gradually narrower with increasing distance from the side of the fabric layer 650. Base portions 622 and 626 are positioned on opposing sides of the opening 660.

Figure 6C:
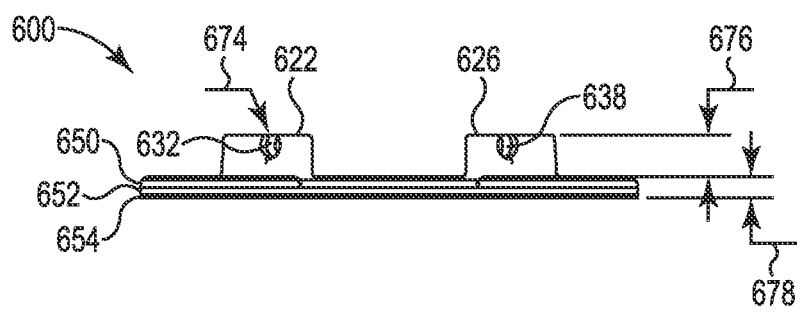
FIG. 6C is a diagram illustrating a side view of the infusion site retainer shown in FIG. 6A after assembly according to one embodiment.

FIG. 6C is a diagram illustrating a side view of the infusion site retainer 600 shown in FIG. 6A after assembly according to one embodiment. As shown in FIG. 6C, each of the trenches 628 and 630 has a radius of curvature 674, which is about 0.191 cm in one embodiment. The base 602 has a thickness 676, which is about 0.584 cm in one embodiment. The support structure 648 has a thickness 678, which is about 0.305 cm in one embodiment.

The infusion site retainers 100, 500, and 600 according to one embodiment set and anchor infusion tubing securely, and allow a healthcare worker to make loops and tubing adjustments, including changing the direction of the tubing, without having to use tape and without having to remove the retainer 100, 500, or 600.

One embodiment is directed to an infusion site retainer configured to maintain tubing coupled to an infusion port. The infusion site retainer includes a base configured to be secured to a patient and comprising a patient surface opposite a first surface, and at least one trench formed in the base to couple the tubing to the base.

The at least one trench according to one embodiment comprises a first trench that includes a first trench portion that extends from a distal end of the base toward a proximal end of the base, and the first trench portion branches into a second trench portion and a third trench portion. The second trench portion is substantially parallel to the first trench portion, and the second trench portion extends from the first trench portion to the proximal end of the base. The third trench portion branches laterally away from first trench portion, and is substantially perpendicular to the first trench portion and the second trench portion, and extends from the first trench portion to a lateral side of the base. In one embodiment, the at least one trench comprises a second trench configured in a same manner as the first trench.

The infusion site retainer according to one embodiment further includes a plurality of locking features that facilitate locking a portion of the tubing in the at least one trench, wherein each of the locking features extends over and covers a portion of the at least one trench.

In one embodiment, the base includes a first lateral base portion, a central base portion, and a second lateral base portion, and wherein the central base portion is positioned between the first lateral base portion and the second lateral base portion, and wherein the first lateral base portion and the second lateral base portion have a larger thickness than the central base portion.

In one embodiment, the infusion site retainer further includes a cover configured to cover the first surface of the base. The cover according to one embodiment includes a first cover portion, a second cover portion, and a semi-cylindrical protrusion positioned between the first cover portion and the second cover portion. In one embodiment, the cover includes a hinge attachment feature that pivotally connects the cover to the base, and the cover is configured to be pivoted via the hinge attachment feature between an open position and a closed position. In one embodiment, the infusion site retainer further includes a clip configured to maintain the cover in the closed position.

In one embodiment, the infusion site retainer further includes at least one trench formed in a bottom surface of the cover. The at least one trench formed in the bottom surface of the cover is aligned with and lies directly over the at least one trench formed in the base when the cover is in a closed position.

In one embodiment, the base includes a first lateral base portion and a second lateral base portion, which are separate and distinct elements, and the infusion site retainer further includes a support structure, wherein the first lateral base portion and the second lateral base portion are positioned on the support structure. The support structure according to one embodiment includes a fabric layer, a clear plastic layer, and a cover layer. A bottom surface of the clear plastic layer comprises an adhesive surface that is covered by the cover layer, and the cover layer is removable by a user to expose the adhesive surface for attachment to a patient. In one embodiment, an opening is formed in one side of the fabric layer, and extends toward and beyond a center of the fabric layer.

In one embodiment, each of the first lateral base portion and the second lateral base portion has a semi-circular shape, with a straight side and a rounded side. The straight sides of the first lateral base portion and the second lateral base portion are parallel and face each other.

Another embodiment is directed to a method of securing tubing coupled to an infusion port. The method includes attaching a base to the patient, and retaining the tubing in at least one trench formed in the base.

Although the present invention has been described with reference to preferred embodiments, workers skilled in the art will recognize that changes can be made in form and detail without departing from the spirit and scope of the present invention.

What is claimed is:

1. An infusion site retainer configured to maintain tubing coupled to an infusion port, the infusion site retainer comprising:
   a base configured to be secured to a patient and comprising a patient surface opposite a first surface;
   at least one trench formed in the base to couple the tubing to the base, wherein the at least one trench comprises a first trench that includes a first trench portion that extends from a distal end of the base toward a proximal end of the base, wherein the first trench portion branches into a second trench portion and a third trench portion, wherein the third trench portion branches laterally away from first trench portion and extends from the first trench portion through a lateral end of the base; and
   a cover configured to cover the first surface of the base, wherein the cover includes a first cover portion, a second cover portion, and a semi-cylindrical protrusion positioned between the first cover portion and the second cover portion.

2. The infusion site retainer of claim 1, wherein the second trench portion extends from the first trench portion to the proximal end of the base.

3. The infusion site retainer of claim 2, wherein the at least one trench comprises a second trench configured in a same manner as the first trench.

4. The infusion site retainer of claim 1, and further comprising a plurality of locking features that facilitate locking a portion of the tubing in the at least one trench, wherein each of the locking features extends over and covers a portion of the at least one trench.

5. The infusion site retainer of claim 1, wherein the base includes a first lateral base portion, a central base portion, and a second lateral base portion, and wherein the central base portion is positioned between the first lateral base portion and the second lateral base portion, and wherein the first lateral base portion and the second lateral base portion have a larger thickness than the central base portion.

6. An infusion site retainer configured to maintain tubing coupled to an infusion port, the infusion site retainer comprising:
   a base configured to be secured to a patient and comprising a patient surface opposite a first surface;
   at least one trench formed in the base to couple the tubing to the base, wherein the at least one trench comprises a first trench that includes a first trench portion that extends from a distal end of the base toward a proximal end of the base, wherein the first trench portion branches into a second trench portion and a third trench portion, wherein the third trench portion branches laterally away from first trench portion and extends from the first trench portion through a lateral end of the base;
   a cover configured to cover the first surface of the base, wherein the cover includes a hinge attachment feature that pivotally connects the cover to the base, and wherein the cover is configured to be pivoted via the hinge attachment feature between an open position and a closed position.

7. The infusion site retainer of claim 6, and further comprising a clip configured to maintain the cover in the closed position.

8. An infusion site retainer configured to maintain tubing coupled to an infusion port, the infusion site retainer comprising:
- a base configured to be secured to a patient and comprising a patient surface opposite a first surface;
- at least one trench formed in the base to couple the tubing to the base, wherein the at least one trench comprises a first trench that includes a first trench portion that extends from a distal end of the base toward a proximal end of the base, wherein the first trench portion branches into a second trench portion and a third trench portion, wherein the third trench portion branches laterally away from first trench portion and extends from the first trench portion through a lateral end of the base;
- a cover configured to cover the first surface of the base, wherein at least one trench is formed in a bottom surface of the cover, wherein the at least one trench formed in the bottom surface of the cover extends from a proximal end of the cover to a distal end of the cover.

9. The infusion site retainer of claim 8, wherein the at least one trench formed in the bottom surface of the cover is aligned with and lies directly over the at least one trench formed in the base when the cover is in a closed position.

10. A method of securing tubing coupled to an infusion port, the method comprising:
- attaching a base to the patient; and
- retaining the tubing in at least one trench formed in the base, wherein the at least one trench comprises a first trench that includes a first trench portion that extends from a distal end of the base toward a proximal end of the base, wherein the first trench portion branches into a second trench portion and a third trench portion, wherein the third trench portion branches laterally away from first trench portion and extends from the first trench portion through a first lateral end of the base, wherein the at least one trench comprises a second trench that includes a first trench portion that extends from the distal end of the base toward the proximal end of the base, wherein the first trench portion of the second trench branches into a second trench portion and a third trench portion, wherein the third trench portion of the second trench branches laterally away from first trench portion of the second trench and extends from the first trench portion of the second trench through a second lateral end of the base.

* * * * *